United States Patent [19]

Mosior et al.

[11] 4,122,856

[45] Oct. 31, 1978

[54] SURGICAL INSTRUMENT AND METHOD OF ASSEMBLY THEREOF

[75] Inventors: Donald J. Mosior, Mundelein, Ill.; Charles D. Cawood, Jr., Houston, Tex.; Michael H. Ekinaka, Irvine, Calif.

[73] Assignee: American Hospital Supply Corporation, Evanston, Ill.

[21] Appl. No.: 730,869

[22] Filed: Oct. 8, 1976

[51] Int. Cl.² ............................................. A61B 17/32
[52] U.S. Cl. .................................... 128/311; 128/2 B; 128/321;
[58] Field of Search ............................................. 29/505 128/311;321;2 B

[56] References Cited

U.S. PATENT DOCUMENTS

| 86,016 | 1/1869 | Howell | 128/321 |
|---|---|---|---|
| 1,127,948 | 2/1915 | Wappler | 128/311 |
| 2,034,785 | 3/1936 | Wappler | 128/321 |
| 2,060,366 | 11/1936 | Dunlap | 128/321 X |
| 2,113,246 | 4/1938 | Wappler | 128/321 |
| 2,518,994 | 8/1950 | Miller | 128/321 |

Primary Examiner—Robert W. Michell
Assistant Examiner—Michael H. Thaler
Attorney, Agent, or Firm—Tilton, Fallon, Lungmus & Chestnut

[57] ABSTRACT

An improved surgical instrument having a sheath, a grasping and/or cutting jaw assembly at one end of the sheath, a housing at the sheath's opposite end, and a plunger slidably supported by the housing and connected to the jaw assembly by means of an actuator rod extending through the sheath. The housing and plunger portions of the instrument are adapted to be coupled to a handle unit, if desired, for manipulation of the instrument and operation of the jaw assembly. The structure and method for facilitating quick removal and replacement of the jaw assembly and actuator rod are disclosed.

12 Claims, 10 Drawing Figures

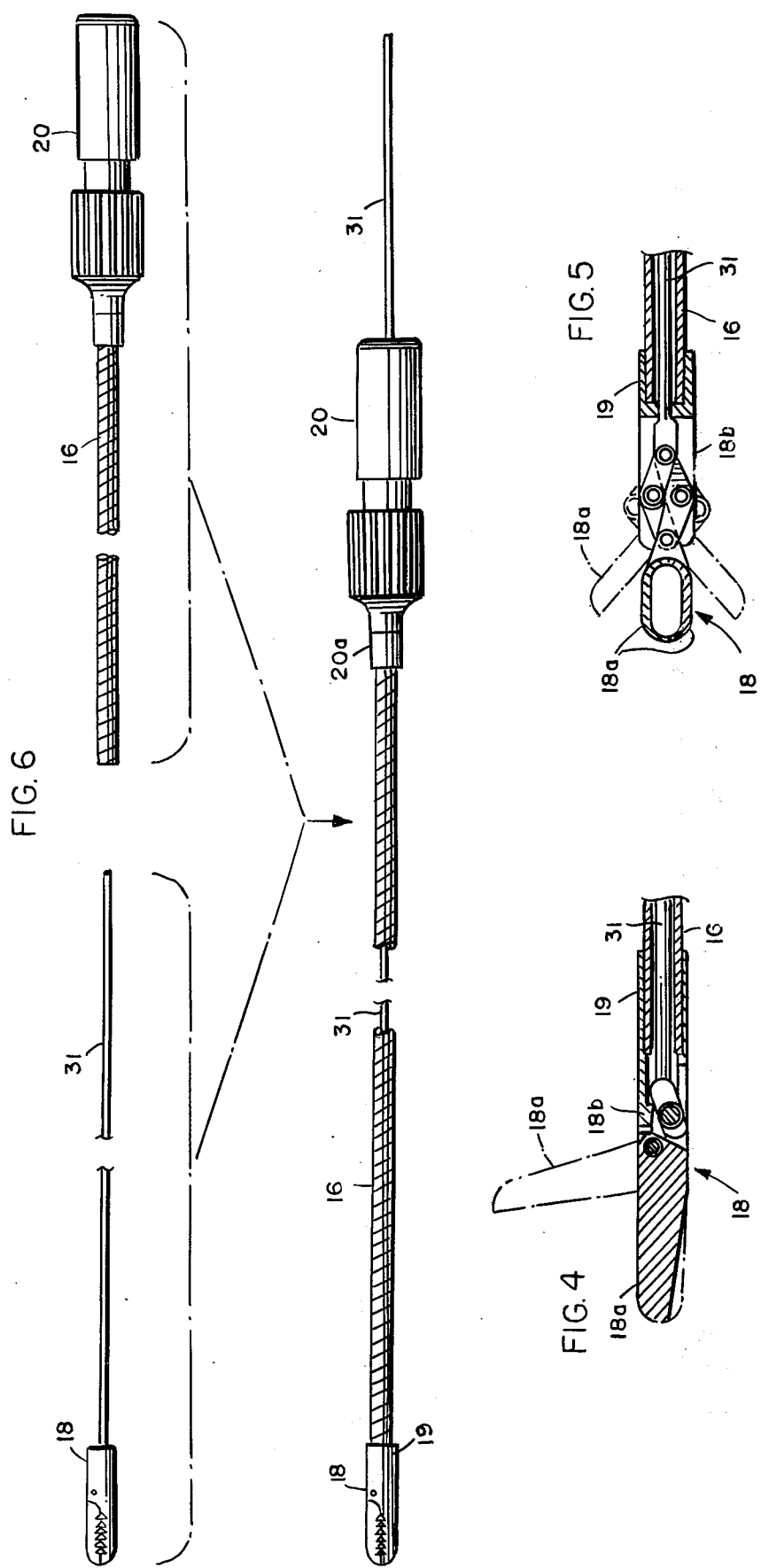

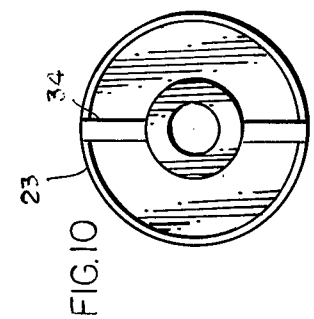
FIG.10
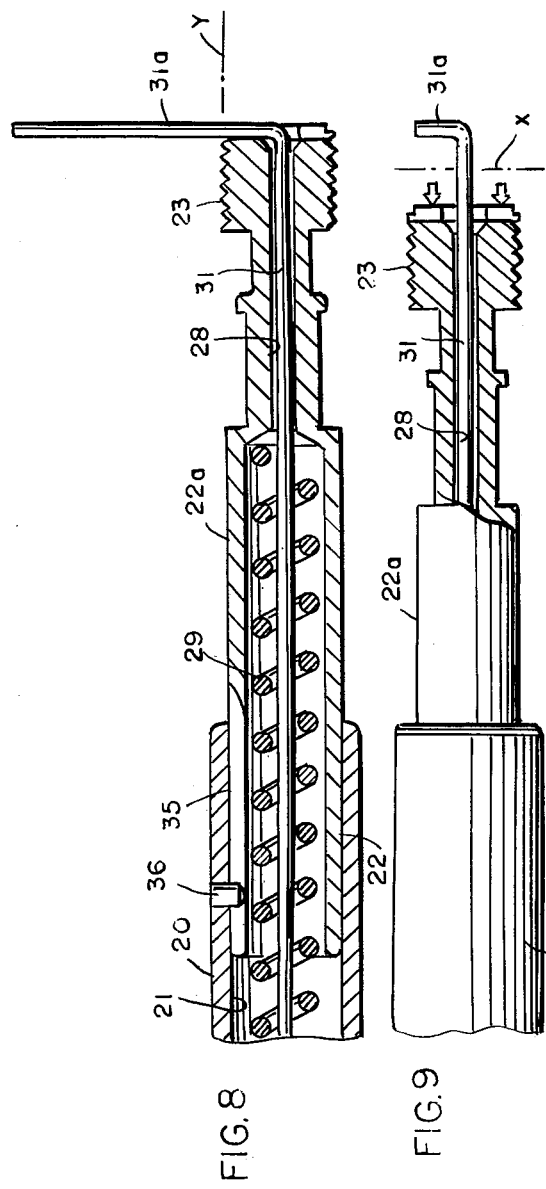
FIG.8
FIG.9
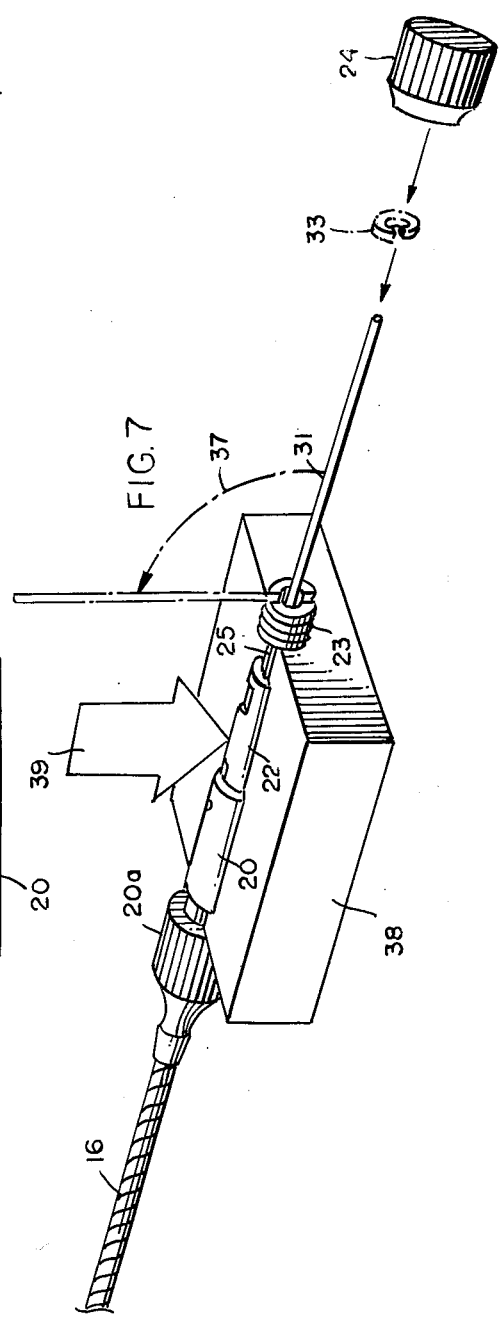
FIG.7

SURGICAL INSTRUMENT AND METHOD OF ASSEMBLY THEREOF

BACKGROUND AND SUMMARY

This invention is concerned with improvements in the construction and method of assembly of a class of miniaturized surgical instruments primarily intended for use in cystoscopic procedures but also suitable or adaptable for other uses such as proctoscopic or bronchoscopic procedures. When adapted for urological use, such instruments are commonly referred to as "flexible instruments" because of the flexible character of the actuating rod and its sheath which permits such an instrument to be fed through a cystoscope sheath and directed in its movement by a deflecting (Albarran) bridge or other suitable means. Using the cystoscope to reveal the area under examination of treatment, the urologist directs the jaw assembly of the flexible instrument to grasp a portion of the tissue or foreign object, take a biopsy specimen, or perform certain types of corrective surgery.

The structural complexity and small size of the jaw assembly, and the manner in which such an instrument is commonly treated along with other less delicate instruments, makes such a jaw assembly particularly vulnerable to damage. Although the jaw assembly constitutes only a small part of the instrument as a whole, jaw damage renders the entire instrument inoperative and, in the past, has generally resulted in an entire instrument being discarded or returned to the manufacturer for factory repair. While hospitals, especially larger hospitals, often have facilities for making limited repairs to surgical instruments, the construction of prior flexible instruments is such that field replacement of a broken or damaged jaw assembly is virtually impossible. Thus, even if a supply of replacement jaw assemblies was available, the job of removing an old assembly and replacing it with a new one, along with the measuring, brazing, soldering, and replating operations that would normally be required, are too difficult or involved to be undertaken by most field repair facilities.

It is therefore a primary object of this invention to provide an improved surgical instrument, and its method of assembly, which permit field replacement of the jaw assembly of that instrument. Such replacement may be performed relatively quickly and easily without complex rebuilding procedures and without brazing, soldering, and replating operations.

Some of the features of the instrument which help to make it field repairable also contribute in making it less likely to become damaged or broken in the first place. For instance, breakage of an actuator rod caused by twisting of that rod is a problem virtually eliminated by the instrument construction of this invention. Also, should excessive force be exerted to urge the jaws of the instrument into closed positions, the excess force will be directed away from the jaws to the coupling of the actuator rod and plunger (where deformation of the rod may be easily repaired), thereby protecting the delicate jaws against accidental damage from the application of excessive force.

Briefly, the instrument comprises an elongated tubular sheath (which, although usually flexible, need not be so), a jaw assembly detachably connected to one end of the sheath and a fixation housing secured to the sheath's opposite end, and a plunger mounted for reciprocation in a chamber provided by the housing. The plunger has an axial bore aligned with the passage of the sheath and an actuation rod extends through the passage and bore and is operatively connected to the jaw assembly. A helical compression spring urges the plunger in a direction extending axial and outwardly from the housing chamber, and stop means are provided by the actuation rod for precisely limiting the extent of outward travel of the plunger under the influence of the spring force without at the same time preventing axial inward movement of the plunger independently of the rod and stop means. A terminal member, preferably in the form of a knob, is threadedly connected to the plunger and secures the plunger against inward axial movement independently of the rod.

In the embodiment illustrated, the stop means takes the form of an end portion of the actuation rod bent at substantially right angles to the remainder of the rod. The laterally turned end portion is received in a radial (or diametric) slot in the end of the plunger and, as already indicated, is maintained in that position by the knob. When the knob is removed, the plunger may be retracted independently of the actuation rod, thereby fully exposing the angular end portion for deactivation of the stop means either by removal, as by cutting off the perpendicular end portion, or by bending that portion back into axial alignment with the remainder of the rod. Upon such deactivation of the stop means, the actuating rod and the jaw assembly to which it is operatively connected may be separated from the remainder of the instrument. Replacement of the jaw assembly and its actuating rod involves the reverse procedure combined with the further steps of first retracting the plunger a limited predetermined distance into the housing and then temporarily holding that plunger precisely in its retracted position, preferably by means of a jig, while the new actuating rod is bent laterally to form the stop means for limiting plunger extension in the assembled instrument.

Other aspects, advantages, and objects of the invention will become apparent from the specification and drawings.

DRAWINGS

FIGS. 4 and 5 are enlarged fragmentary longitudinal sectional views of alternate jaw styles used for cutting and biopsy procedures, respectively.

FIG. 6 is a longitudinal view taken partly in section, showing the rod-jaw assembly and sheath-housing assembly when such components are assembled and disassembled.

FIG. 7 is a perspective view depicting certain steps in the method of assembly of the instrument.

FIG. 8 is a fragmentary sectional view illustrating the relationship of parts at the completion of one of the procedural steps.

FIG. 9 is a view similar to FIG. 5 but showing the relationship of parts during another procedural step.

FIG. 10 is a greatly enlarged end view of the plunger of the instrument.

DETAILED DESCRIPTION

Figure 1:
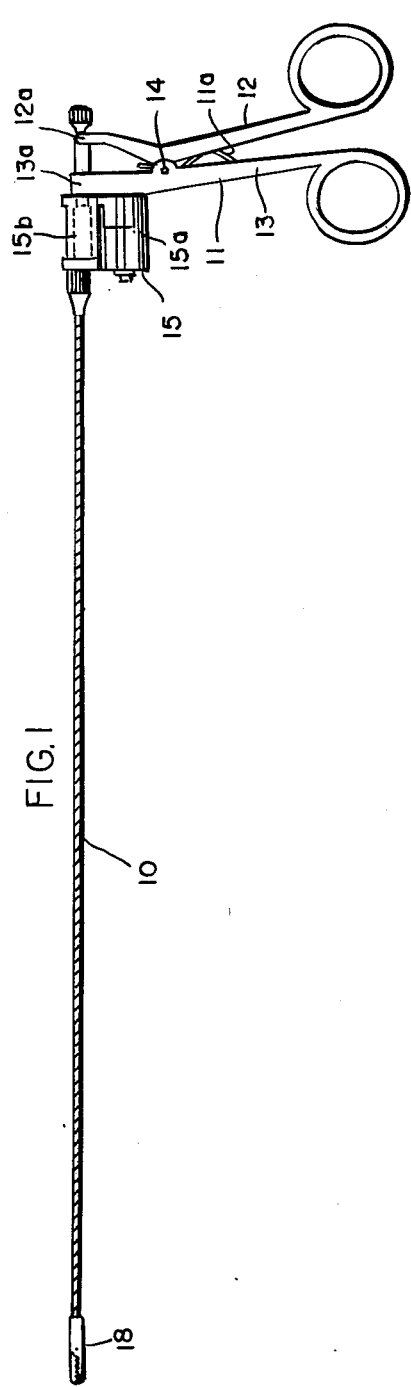
FIG. 1 is a side elevational view of a surgical instrument connected to a handle unit to form the complete combination as it would be used in performing surgical procedures.

FIG. 1 depicts an instrument assembly 10 detachably connected to a handle assembly 11 to form an instrument-handle combination useful in performing urological procedures and other surgical procedures. The handle assembly 11 is shown only for illustrative purposes; it does not constitute a part of the present invention although its relationship to the instrument 10 does reveal the reasons for certain structural features of that instrument. For a more detailed disclosure of the handle assembly 11, reference may be had to co-pending co-owned application Ser. No. 730,870, filed Oct. 8, 1976, now U.S. Pat. No. 4,084,594.

Briefly, the handle assembly comprises a pair of handles 12 and 13 connected by pivot pin 14. The stationary handle 13 supports a wing lock assembly 15 which takes the form of a pair of wing lock members functioning to latch the instrument in place. When the parts are latched together as illustrated in FIG. 1, manipulation of the handles causes the fork portion 12a to move towards and away from the fork portion 13a to control the jaws of the instrument. The instrument may be disconnected from the handle assembly by simply squeezing together the lower wing portions 15a of the wing lock assembly, causing the clamping portions 15b to spread apart and permit the instrument to be lifted free of the handle assembly. Instrument attachment is accomplished by reversing the procedure, such attachment being further simplified by forming the wing lock members with cam surfaces which cause the clamping portions 15b to be cammed apart as the instrument is forced downwardly between the wing lock members. A positioning spring 11a between the handles 12 and 13 insures proper alignment of the fork portion 12a and the portion 25 of the plunger 22 received thereby.

Figure 2:
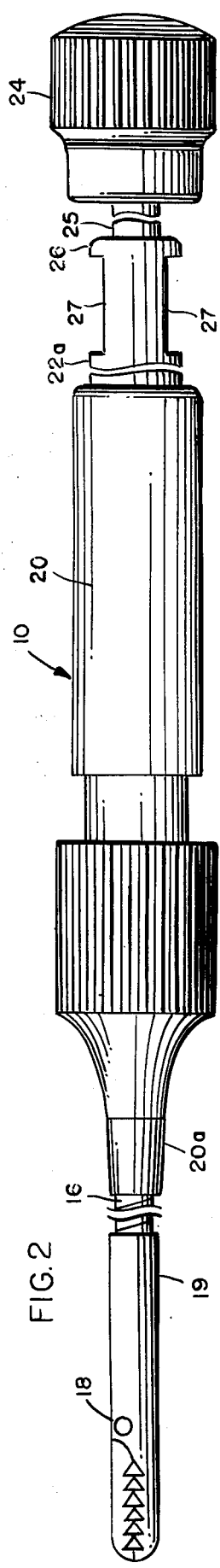
FIG. 2 is an enlarged broken side elevational view of the instrument itself.
Figure 3:
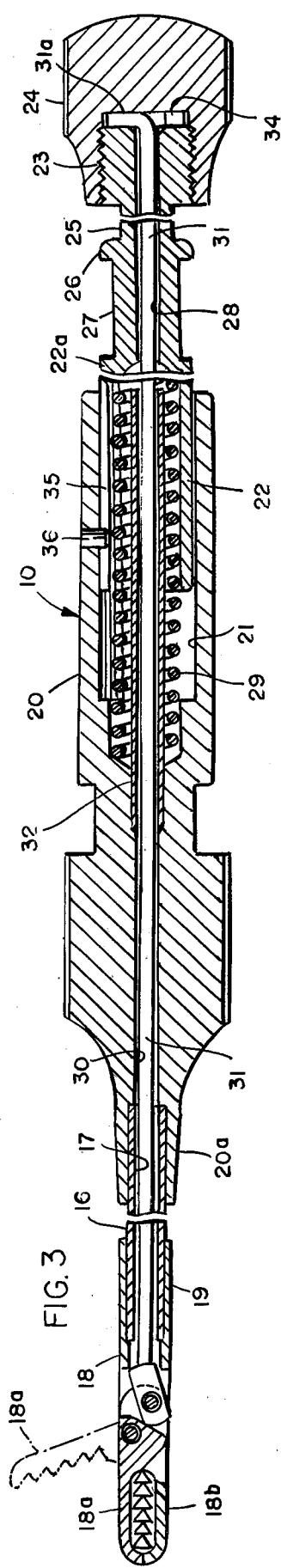
FIG. 3 is an enlarged longitudinal sectional view of the instrument shown in FIG. 2.

The instrument 10 is shown in greater detail in FIGS. 2 and 3. It includes an elongated tubular sheath 16 which has a passage 17 extending therethrough and which may be formed either as a flexible member or as a relatively rigid member. Ordinarily such a sheath would be flexible so that it might be flexed or directed by a deflecting bridge used in conjunction with a cystoscope; however, it is not essential that the sheath be flexible and for some applications a relatively rigid sheath may be preferred.

A jaw assembly 18 is secured to the sheath at its distal end. One form of clamping jaw assembly is illustrated in FIGS. 2 and 3, the assembly including a movable jaw 18a and a fixed jaw 18b. It is to be understood, however, that other types of jaw assemblies are known and may be provided such as, for example, a scissor jaw assembly (FIG. 4), a biopsy specimen cutting jaw assembly (FIG. 5), and the like.

At its proximal end, the jaw assembly, whatever its type, takes the form of a tubular sleeve 19 which snugly receives the distal end of sheath 16 (FIG. 3). The sleeve 19 is crimped or swaged slightly to hold it upon the sheath against axial and rotational movement without, at the same time, preventing forceful detachment of the jaw assembly from the sheath when repair of an instrument is undertaken in the manner set forth hereinafter.

The proximal end of sheath 16 is secured within the nose portion 20a of fixation housing 20, preferably by swaging in a manner similar to that for securing the jaw assembly 18 to the sheath. As shown in FIG. 3, the fixation housing includes a plunger chamber 21 which slidably and reciprocably receives plunger 22. A stem portion 22a of the plunger extends a substantial distance proximally from the open end of bore 21, the stem terminating in an externally-threaded head portion 23 upon which a knob 24 is fitted. The stem also includes a fork receiving portion 25 of square cross sectional configuration adapted to be received in any of four 90° positions within the fork portion 12a of movable handle 12. Just distally of the fork-receiving portion is a shoulder 26. The remaining portion of the exposed stem may have a pair of flats 27 to facilitate holding of the stem during assembly and disassembly of the instrument.

The plunger 22 has an axial bore 28 which is enlarged within the cylindrical body portion at the plunger's distal end to receive a helical compression spring 29. The spring urges the plunger axially and outwardly (or proximally), in a direction to the right as illustrated in FIG. 3. The axial bore 28 of the plunger communicates with an axial bore 30 which extends through the nose of the housing and which constitutes an extension of the chamber of that housing. Bore 30 in turn communicates directly with the passage 17 of sheath 16.

An actuation rod 31 extends through the passage of the sheath and is operatively connected to the jaw assembly 18. The rod continues proximally or inwardly through the housing and through the bore 28 in plunger 22. If desired, a guide tube 32 may be secured to the housing within chamber 21 to reduce or prevent flexing movement of the rod within the chamber 21 and to prevent contact between the rod and spring 29.

When the parts are assembled as shown in FIGS. 2 and 3, spring 29 is in a state of partial compression, exerting a force which urges plunger 22 outwardly (to the right). The extent of such outward travel of the plunger is limited, however, by stop means which, in the illustration given, takes the form of a laterally bent portion 31a at the proximal end of actuation rod 31. Thus, the laterally bent stop portion not only precisely limits the extent of outward travel of the plunger 22, but also results in the jaws of the jaw assembly 18 normally being held in closed positions under the preload force of compression spring 29. It is to be noted that although the stop portion 31a of the actuation rod limits outward movement of the plunger 22, it does not of itself prevent axial inward movement of that plunger (see FIG. 9). Such limitation against independent inward movement of the plunger (i.e., independently of rod 31) results from the knob or terminal member 24 which is threaded upon the head of the plunger and which engages stop member 31a to secure or clamp the stop member between the plunger and the knob. If desired, a suitable lock washer 33 may be disposed within the knob to hold the knob tightly in place. The laterally turned stop portion 31a of the rod is received in one of two radial channels or grooves 34 formed in the outer end face of the plunger.

Since the laterally turned end portion 31a of the rod is received in a channel 34, the rod and plunger are locked together against independent relative rotation. If the plunger were free to rotate within chamber 21, rod 31 could twist and such twisting action would tend to reduce both its operative life and its effective length. Therefore, to prevent rotation of the plunger within the housing, the body portion of the plunger disposed within the chamber 21 has a longitudinal groove 35 which receives a guide pin 36 projecting inwardly from the wall of the housing (FIG. 3).

The instrument as described is easily assembled during production and may be readily disassembled and reassembled when repair or replacement of a jaw and actuating rod assembly is necessary. Assuming that replacement of a jaw assembly is required, knob 24 is first unthreaded from the end of the plunger. Removal of the knob may be facilitated by gripping the stem of the plunger (at flats 27) between the jaws of a wrench or other suitable tool to hold the plunger and the instrument against rotation during knob rotation. Once the knob has been removed, the plunger is depressed as shown in FIG. 9 to expose the laterally-turned end portion of the rod. Using wire clippers, the rod is cut along line x to detach the laterally-turned stop portion 31a from the rest of the rod. Upon such detachment of the stop portion, the plunger may if necessary be removed from its chamber for cleaning or repair. In any event, after the laterally-turned stop portion has been detached from (or straightened in relation to) the remainder of the rod, plunger 22 is free to travel axially outwardly by reason of the force exerted by compression spring 29.

Following detachment of the laterally-turned stop portion 31a of the rod, the operator then grips the jaw assembly 18 with a suitable pliers or holding tool and pulls it axially from the sheath, removing both the jaw assembly and the actuating rod connected thereto (FIG. 6). The replacement jaw-rod assembly is attached by a reversal of the same procedure by using crimping pliers or other suitable device to securely swage and/or crimp the new jaw assembly onto the sheath. The actuator rod of the replacement unit would be straight and substantially longer than necessary for use in the completely-repaired instrument. The rod is simply fed through the passage of the sheath, into the chamber 21 of the housing, and through the bore 28 of the plunger. The plunger must then be retracted a limited extent into the housing and held in that position as the elongated projecting end portion 31a of the rod is bent laterally as indicated by arrow 37 in FIG. 7. Such precise positioning of the plunger in a partially retracted position, and the holding of the plunger in that position during bending of the rod, is essential because when the parts are fully assembled the maximum extension of the rod must be such that quick coupling of the instrument to the instrument handle 11 may be readily achieved. Since the fork portions 12a and 13a of the instrument handle assume neutral positions with a predetermined spacing therebetween, that spacing must be matched by the maximum extension of the plunger if the parts are to fit together and operate properly.

To facilitate the step of partially retracting the plunger to a position which will ultimately become the plunger's position of maximum extension, and to hold the plunger in that partially-retracted position during bending of the rod, a suitable jig 38 may be used (FIG. 8). The jig as shown has a recess for removably receiving a portion of the housing and the plunger, the instrument being fitted into the recess in the direction indicated by arrow 39. While the instrument is so held, the extended portion of the wire is bent laterally until the parts assume the relationship illustrated in FIG. 8. Thereafter, the laterally projecting portion of the rod is severed along line y, preferably by first retracting the plunger to a greater extent as shown in FIG. 6. The knob is replaced upon the head of the plunger to complete the instrument assembly procedure.

It is believed apparent that if replacement of a sheath is required, in addition to replacement of a jaw assembly, then a similar procedure is followed except that the old sheath is disconnected from the housing and a new sheath is swaged or otherwise secured in place. Thereafter, the new jaw-rod assembly is installed as described.

By forming the stop means as a lateral bend 31a in rod 31, it has been found that the likelihood of jaw damage because of excessive closing force applied through the handles is reduced. The application of excessive force to close the jaws, or to hold them in closed condition, tends to cause a straightening of bent portion 31a before enough force is transmitted to the jaws to damage them. The preferential stripping of the rod from the plunger protects the jaws and may be easily repaired simply by removing the knob, inserting the instrument into the jig as shown in FIG. 7, reforming the bend 31a, and then replacing the knob (and lock washer 33, if used).

While in the foregoing we have disclosed the structure and method of the invention in considerable detail for purposes of illustration, it will be understood by those skilled in the art that many of these details may be varied without departing from the spirit and scope of the invention.

We claim:

1. A surgical instrument comprising an elongated tubular sheath having a passage therethrough, a jaw assembly detachably connected to said sheath at one end thereof, a fixation housing secured to the opposite end of said sheath, said housing having a plunger chamber communicating with said passage, a plunger disposed within said chamber and having an axial bore therethrough aligned with said passage, an actuation rod extending through said passage and bore and operatively connected at one end to said jaw assembly, spring means urging said plunger in a direction extending axially and outwardly from said chamber, stop means at the outer end of said rod opposite from said one end thereof, said stop means projecting laterally relative to the axis of said plunger and normally engaging the plunger's outer end for precisely limiting the extent of outward travel of said plunger without preventing axial inward movement of said plunger independently of said rod and stop means, said outer end of said plunger being externally threaded, and a terminal member detachably connected to said plunger and having a recess receiving both said outer end of said plunger and said stop means, said terminal member being internally threaded for threadedly receiving the plunger's outer end and confining said stop means within said recess to secure said plunger and rod against independent axial movement, said stop means being separable from said rod and being exposed for separation when said terminal member is detached, whereby, upon detachment of said terminal member from said plunger, said plunger may be shifted inwardly independently of said rod to permit removal of said stop means, and upon removal of said stop means, said jaw assembly may be detached from said one end of said sheath and said actuation rod may be axially withdrawn from said housing and plunger.

2. The instrument of claim 1 in which said spring means comprises a helical compression spring disposed and normally concealed within said chamber of said housing and said bore of said plunger.

3. The instrument of claim 2 in which said terminal member comprises a knob.

4. The instrument of claim 1 in which said stop means is formed integrally with said rod and comprises a laterally-turned extension of said rod.

5. The instrument of claim 4 in which said plunger is provided with an end surface having a transversely-extending groove receiving said laterally-turned extension of said rod.

6. The instrument of claim 5 in which a lock washer is interposed between said terminal member and said laterally-turned extension of said rod.

7. The instrument of claim 6 in which said terminal member comprises a knob.

8. The instrument of claim 4 in which said terminal member comprises a knob.

9. The instrument of claim 1 in which said terminal member comprises a knob.

10. The instrument of claim 1 in which locking means is provided by said housing and plunger for preventing rotation of said plunger within said chamber.

11. The instrument of claim 10 in which said locking means comprises a longitudinal channel in said plunger and a projection secured to said housing within said chamber and slidably received in said channel.

12. The instrument of claim 1 in which said plunger has a non-cylindrical surface portion disposed outwardly beyond said housing.

* * * * *